(12) United States Patent
Savage et al.

(10) Patent No.: US 10,494,400 B2
(45) Date of Patent: Dec. 3, 2019

(54) HEPATITIS C VIRUS INHIBITORS

(71) Applicant: BRISTOL-MYERS SQUIBB COMPANY, Princeton, NJ (US)

(72) Inventors: Scott A. Savage, Yardley, PA (US); Nathan R. Domagalski, Clinton, NJ (US); Brendan Mack, New Brunswick, NJ (US); Purushotham Vemishetti, Monmouth Junction, NJ (US); Yuping Qiu, Princeton Junction, NJ (US); Michael Fenster, New York, NY (US); Daniel M. Hallow, Bishop, GA (US); Glenn Ferreira, Newark, DE (US); Amanda Rogers, Piscataway, NJ (US); Sha Lou, North Brunswick, NJ (US); Lindsay Hobson, Kendall Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/317,555

(22) PCT Filed: Jun. 23, 2015

(86) PCT No.: PCT/US2015/037153
§ 371 (c)(1),
(2) Date: Dec. 9, 2016

(87) PCT Pub. No.: WO2015/200305
PCT Pub. Date: Dec. 30, 2015

(65) Prior Publication Data
US 2018/0155393 A1    Jun. 7, 2018

Related U.S. Application Data

(60) Provisional application No. 62/016,952, filed on Jun. 25, 2014.

(51) Int. Cl.
*C07K 5/083* (2006.01)
*C07K 5/062* (2006.01)
*C07K 1/02* (2006.01)

(52) U.S. Cl.
CPC .............. *C07K 5/0808* (2013.01); *C07K 1/02* (2013.01); *C07K 5/06034* (2013.01)

(58) Field of Classification Search
CPC ..... C07K 1/02; C07K 5/06034; C07K 5/0808
See application file for complete search history.

(56) References Cited

U.S. PATENT DOCUMENTS

| | | |
|---|---|---|
| 7,449,479 B2 | 11/2008 | Wang et al. |
| 7,915,291 B2 | 3/2011 | Wang et al. |
| 8,299,094 B2 | 10/2012 | Wang et al. |
| 8,507,722 B2 | 8/2013 | Wang |
| 8,710,229 B2 | 4/2014 | Wang et al. |
| 8,889,871 B2 | 11/2014 | Wang et al. |
| 9,227,940 B2 | 1/2016 | Wang et al. |
| 9,636,375 B2 | 5/2017 | Wang et al. |

FOREIGN PATENT DOCUMENTS

| | | |
|---|---|---|
| WO | WO 2003/099274 A1 | 12/2000 |
| WO | WO 2009/085659 A1 | 7/2009 |

OTHER PUBLICATIONS

Coupling Reagents (available online at: http://www.biocis.u-sud.fr/IMG/pdf/Coupling_Reagents.pdf, captured on Feb. 7, 2012. (Year: 2012).*

Akbar et al., "Evaluating the Role of Macrocycles in the Susceptibility of Hepatitis C Virus NS3/4A Protease Inhibitors to Drug Resistance," ACS Chemical Biology, vol. 8, No. 7, pp. 1469-1478 (2013).

Scola, et al., "The Discovery of Asunaprevir (BMS-650032), An Orally Efficacious NS3 Protease Inhibitor for the Treatment of Hepatitis C Virus Infection," Journal of Medicinal Chemistry, vol. 57, No. 5, pp. 1730-1752 (2014).

* cited by examiner

*Primary Examiner* — Kaipeen E Yang
(74) *Attorney, Agent, or Firm* — Mintz Levin Cohn Ferris Glovsky and Popeo, P.C.

(57) ABSTRACT

The present disclosure relates to methods for making asunaprevir, useful treatment of Hepatitis C virus (HCV) infection, and its intermediates.

2 Claims, No Drawings

HEPATITIS C VIRUS INHIBITORS

CROSS-REFERENCE TO RELATED APPLICATIONS

This application claims priority to U.S. Provisional Patent Application Ser. No. 62/016,952, filed Jun. 25, 2014, which is incorporated by reference in its entirety.

The present disclosure relates to methods for making asunaprevir, useful in the treatment of Hepatitis C virus (HCV) infection, and its intermediates.

Approximately 170 million people worldwide are chronically infected with hepatitis C virus (HCV), including approximately 4 million in the United States. The majority of individuals infected progress to chronic hepatitis, which can lead to cirrhosis, liver failure, and hepatocellular carcinoma (HCC). HCV is the leading indication for liver transplantation in most countries and a major cause of HCC.

There are 6 major HCV genotypes with many subtypes based on sequence heterogeneity of the genome. Genotypes (GT) 1-3 have a worldwide distribution (with GT-1 being the major genotype in the United States, Europe, Japan, and South America), GTs-4 and -5 are found principally in Africa, and GT-6 is distributed primarily in Asia. Although genotype does not predict the outcome of infection, different GT are associated with differential responses to treatment, and allow dosage of current interferon (IFN)-based treatment to be tailored to the GT being treated.

Two first generation direct-acting antiviral agents (DAAs), the HCV protease inhibitors, telaprevir (TVR) and boceprevir (BOC), were approved in the US and EU in 2011 for the treatment of GT 1 chronic hepatitis C (CHC). These regimens have been considered the standard of care for treating GT-1 CHC in countries where they are available. Both regimens have demonstrated improved treatment outcomes compared with IFNα/Ribavirin (RBV) and also offer potentially shorter duration of therapy (24 weeks vs. 48 weeks). However, both these agents must be administered with pegylated interferon-alpha (pegIFNα+RBV), and are therefore associated with the known adverse effects of the IFN/RBV backbone, potentially limiting their overall effectiveness.

Recently, two second generation DAAs, sofosbuvir (SOF) and simeprevir (SMV) have demonstrated Phase 3 efficacy results exceeding those of BOC or TVR when used in combination with PegIFN/RBV and have been approved in the US offering new treatment options to patients with CHC. These new agents are quickly being adopted as the new standard of care, specifically in the US per the American Association for the Study of Liver Diseases (AASLD) and the Infectious Diseases Society of America (IDSA) HCV treatment guidelines. Treatment with SOF also offers a shorter treatment duration of 12 weeks for patients who are GT-1, -2, or -4. Though pegIFNα/RBV free regimens are forthcoming, all of these agents (including SOF, and SMV) are currently approved for use with pegIFNα/RBV in GT-1 patients, and therefore, have the known adverse effects of IFN and RBV. The requirement for pegIFNα/RBV limits the effectiveness of such DAA regimens, particularly in subjects with poor prior virologic response to pegIFNα/RBV and those who cannot tolerate pegIFNα/RBV therapy.

Chronic HCV patients can be effectively treated with IFN and ribavirin sparing Direct Acting Antiviral (DAA) regimens and the ability to decrease treatment duration has been demonstrated with combination use of multiple highly effective DAAs that are able to strongly inhibit the viral replication life cycle. The combination of two or more DAAs without interferon has been shown in multiple different studies to decrease the length of therapy while increasing the number of patients that achieve SVR.

Clinical data demonstrate potent in vivo antiviral activity of a dual regimen containing daclatasvir (DCV) and asunaprevir (ASV). With the success of this regimen, an efficient, commercially viable synthesis of each component is needed. The subject application describes an improved synthesis of asunaprevir and its preceding intermediate.

In a first aspect the present disclosure provides a process for preparing a compound of formula (I),

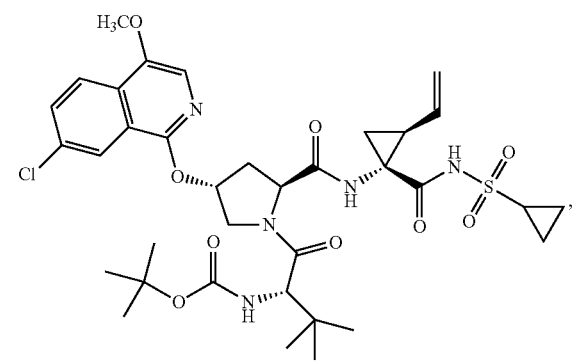

the process comprising:
(a) treating a compound of formula (II),

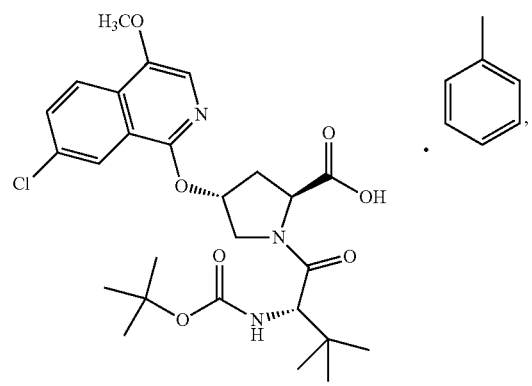

with a compound of formula (V)

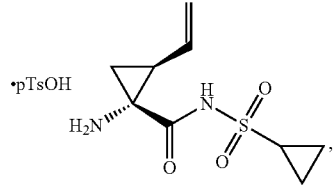

and 1-ethyl-3-(3-dimethylaminopropyl)carbodiimide in the presence of diisopropylethylamine; and
(b) crystallizing the compound of formula (I).

In a first embodiment of the first aspect the process further comprises treating the reaction mixture of step (a) with water and methyl tert-butyl ether. In a second embodiment the process further comprises distilling the isolated organic phase. In a third embodiment the process further comprises seeding the isolated organic phase with crystals of the compound of formula (I).

In a second aspect the present disclosure provides a process for preparing a compound of formula (II),

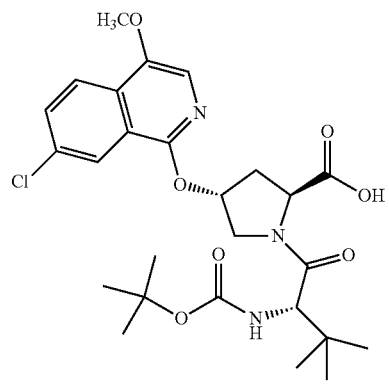
(II)

the process comprising:
(a) treating a compound of formula (III)

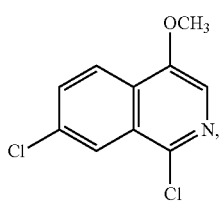
(III)

with a compound of formula (IV)

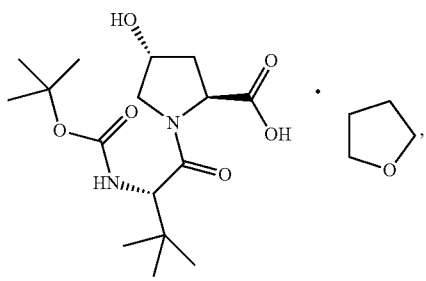
(IV)

in the presence of potassium tert-butoxide; and
(b) crystallizing the product of step (a) from toluene.

In a first embodiment of the second aspect the process further comprises quenching step (a) with sodium phosphate monobasic. In a second embodiment the process further comprises distilling the isolated organic phase. In a third embodiment the process further comprises treating the organic phase with acetic acid and then seeding it with crystals of the compound of formula (II).

In a third aspect the present disclosure provides a process for preparing a compound of formula (I),

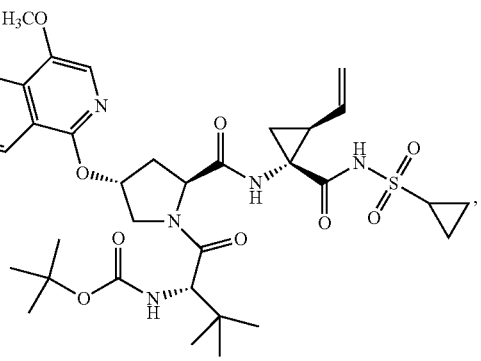
(I)

the process comprising:
(a) treating a compound of formula (III)

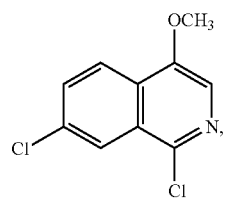
(III)

with a compound of formula (IV)

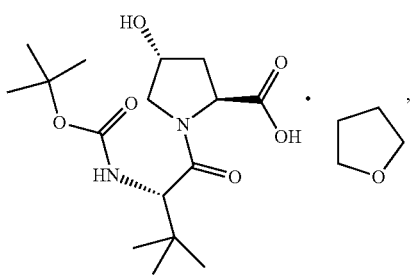
(IV)

in the presence of potassium tert-butoxide; and
(b) crystallizing the product of step (a) from toluene, to form a compound of formula (II)

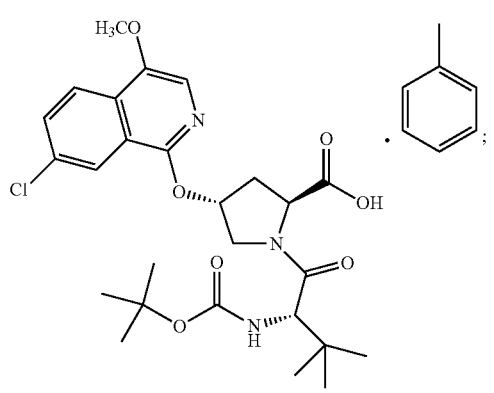

(c) treating the compound of formula (II) with a compound of formula (V)

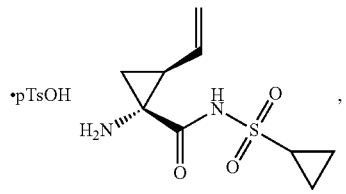

and 1-ethyl-3-(3-dimethylaminopropyl)carbodiimide in the presence of diisopropylethylamine; and
(d) crystallizing the compound of formula (I).

In a fourth aspect the present disclosure provides a process for preparing a compound of formula (I),

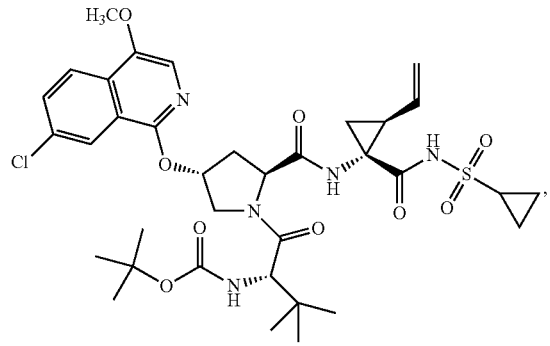

the process comprising:
(a) treating a compound of formula (III)

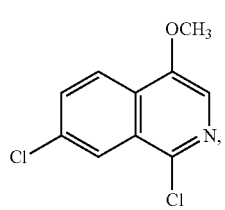

with a compound of formula (IV)

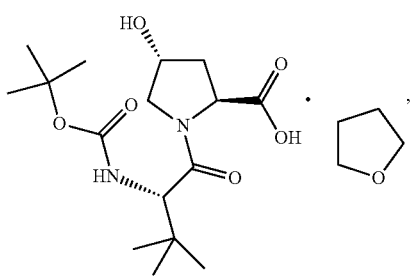

in the presence of potassium tert-butoxide;
(b) quenching step (a) with sodium phosphate monobasic;
(c) isolating then distilling the organic phase of step (b); and
(d) crystallizing the product of step (a) from toluene, to form a compound of formula (II)

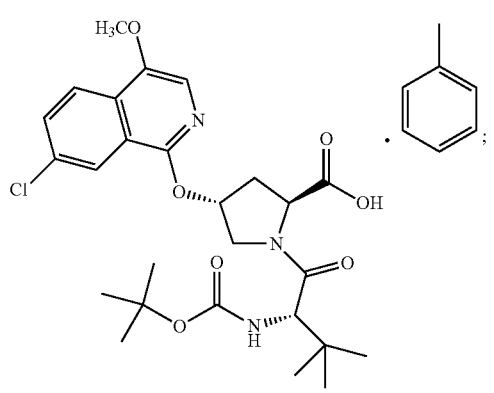

(e) treating the compound of formula (II) with a compound of formula (V)

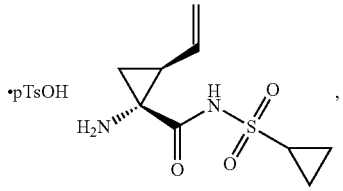

and 1-ethyl-3-(3-dimethylaminopropyl)carbodiimide in the presence of diisopropylethylamine;
(f) treating the reaction mixture of step (e) with water and methyl tert-butyl ether;
(g) isolating then distilling the organic phase of step (f); and
(h) crystallizing the product of step (f) to form the compound of formula (I).

Other aspects of the present disclosure may include suitable combinations of embodiments disclosed herein.

Yet other aspects and embodiments may be found in the description provided herein.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The abbreviations used in the present application, including particularly in the illustrative examples which follow, are well-known to those skilled in the art. Some of the abbreviations used are as follows: THF for tetrahydrofuran; EtOAc for ethyl acetate; MeTHF for 2-methyltetrahydrofuran; min for minutes; NMP for N-methylpyrrolidinone; MeOH for methanol; MTBE for methyl tert-butyl ether; and pTSA for para-toluenesulfonic acid.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

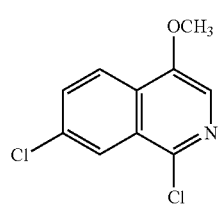 [SMILES: COc1cnc(Cl)c2cc(Cl)ccc12]

Preparation of Compound III

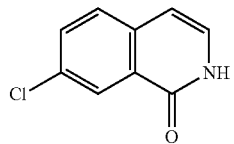 [SMILES: O=c1[nH]ccc2ccc(Cl)cc12]

Step 1—Preparation of Compound A

A reactor charged with 5-chloro-2-methylbenzoic acid (1.0 equiv., limiting reagent), 2-methyltetrahydrofuran (7 L/kg), dimethylformamide (0.02 equiv.) was stirred until a homogeneous solution was obtained. Oxalyl chloride (1.2 equiv.) was added and the solution was agitated at 20° C. for at least 1 h until the formation of the acid chloride was deemed complete by HPLC. In a separate reactor 2-methyltetrahydrofuran (5 L/kg) was treated with aqueous ammonia (25 wt %, 7.0 equiv.), water (3 L/kg) and the temperature set to 30° C. To this solution was added the solution of the acid chloride and the mixture was agitated for 30 min at 35° C. The aqueous layer was separated and the organic layer was washed with a brine solution (16 wt %, 5 L/kg). The organic layer was distilled to 50% of its volume maintaining the temperature <60° C. Continued to distill, maintaining a constant volume by the addition of toluene, until the KF of the solution was <0.1%. To this solution was added dimethylformamide-dimethylacetal (1.10 equiv.) and the mixture was heated to 85° C. and held for at least 3 h until formation of the amidine was deemed complete. On completion of the reaction, the solvents were removed by atmospheric distillation. The distillation was complete when the temperature reached 100° C., then the solution was cooled to 83° C. and transferred to a reactor containing a 85° C. solution of toluene (4 L/kg) and potassium t-amylate solution (25 wt % in toluene, 2 equiv.) and held at 85° C. until the reaction was deemed complete by HPLC. Cooled to 50° C. and charged with MeOH (0.38 L/kg) and distilled to ~40% of the original volume. Cooled to 25° C. and charged with heptane (3.2 L/kg) followed by a mixture of N-methylpyrrolidine and water (7.2 L/kg:7 L/kg). Agitated the biphasic mixture for 30 min then separated the phases. To the aqueous layer was charged conc. HCl until the pH was between 7 and 8. To the slurry that formed was added water (5 L/kg). Filtered the slurry and washed with NMP/water (1 L/kg: 4 L/kg) followed by water (2×2.5 vol). Dried the cake at 50° C. until the KF was <0.5%. The product was obtained as a light yellow solid in 85% yield and >99.5 AP.

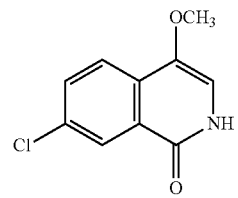 [SMILES: COc1c[nH]c(=O)c2cc(Cl)ccc12]

Step 2—Preparation of Compound B

A reactor charged with iodosobenzenediacetate (1.1 equiv.) and MeOH (10 L/kg) was heated to 30° C. to obtain a homogeneous solution and then cooled to 20° C. A second reactor was charged with Compound A (1.0 equiv., limiting reagent), MeOH (10 L/kg) and methanesulfonic acid (1.5 equiv.). To this mixture was added the solution of iodosobenzenediacetate maintaining the temperature <25° C. Heated the resulting solution to reflux (~65° C.) for ~2 h until the reaction was determined to be complete by HPLC. Removed the methanol by distillation until the volume was ~60% of the original volume. Cooled the batch to 15° C. and added water (8.6 L/kg) followed by aqueous NaOH (25 wt %, 1.5 equiv.) to reach a pH between 5.5 and 7.5. Agitated the slurry for 30 min and filtered. Washed the cake with MeOH/water (1.7 L/kg 2.3 L/kg) followed by water (2×2.3 L/kg). The cake was dried at 50° C. until the LOD was <15%. Charged the crude material to a reactor followed by n-heptane (6.3 L/kg) and heated the slurry to 60° C. for 3 h to remove iodobenzene. Cooled the slurry to 20° C., filtered and washed the cake with n-heptane (2.6 L/kg). Dried the cake at 50-60° C. under vacuum until the iodobenzene was removed. The product was obtained as an orange to brown solid in ~87% yield and >97% purity.

Step 3—Preparation of Compound III

A reactor charged with Compound B (1.0 equiv., Limiting reagent) and toluene (6.5 L/kg) was heated to 80° C. Charged phosphorus oxychloride (1.8 equiv.) and heated the mixture to 100° C. for at least 4 h until the reaction was deemed complete by HPLC. Cooled the reaction mixture to 20° C. and added to an aqueous solution of potassium phosphate tribasic (4.8 kg/kg of potassium phosphate tribasic and water, 10 L/kg). Rinsed the reaction vessel with THF (7.7 kg/kg) and transferred to the quenched biphasic mixture and stirred for 1 h at 20° C. Separated the layers and charged charcoal (0.1 kg/kg) to the organic layer and agitated for 30 min. Removed the charcoal by filtration and washed with THF (1 kg/kg). Washed the organic solution with water (5 L/kg), separated the layers and filtered the organic phase. Distilled the organic phase to an endpoint of 3 L/kg. Heated the slurry to 80° C. to obtain a solution. Charged n-heptane (5 kg/kg) maintaining the temperature >65° C. during the addition. Cooled the slurry to 25° C., stirred for 2 h, then cooled to 0° C. over 2 h and stirred for an additional 2 h. Filtered the slurry and washed the cake with n-heptane (4 L/kg). Dried the cake at 50° C. under vacuum until the LOD was <1.0%. The product was obtained as a white to pale yellow solid in ~86% yield and >99 AP.

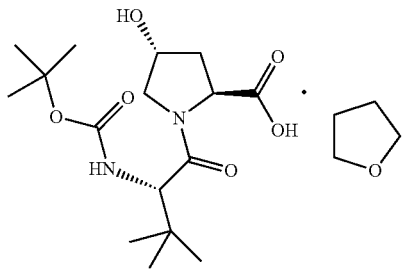

Preparation of Compound (IV)

To a solution of N-Boc-L-tert-leucine (1.0 equiv., limiting reagent) in tetrahydrofuran (3.4 kg/kg) cooled to −5° C. was added diisopropylethylamine (3.10 equiv.) such that the temperature was maintained at <5° C. To this mixture was added methanesulfonyl chloride (1.01 equiv.) while the temperature was maintained at <5° C. and agitated for 1 h to generate the oxazolone intermediate. To this mixture was added a solution of trans-4-hydroxy-L-proline (1.01 equiv.) in water (3.6 kg/kg) while maintaining the temperature at <5° C. The solution was agitated at 0-5° C. until the coupling reaction was deemed complete by HPLC (<1.0 RAP of oxazolone versus Compound IV). Upon completion, the reaction mixture was distilled until the volume was reduced by ~50%. The batch temperature was adjusted to 15° C. and charged with ethyl acetate (9 kg/kg), followed by water (3.6 kg/kg). The mixture was charged with 35 wt % HCl (0.48 kg/kg) until the reaction mixture was pH 3. The phases were allowed to separate and the aqueous phase was removed. The aqueous phase was extracted with ethyl acetate (4.5 kg/kg). The combined ethyl acetate phases were washed with 20 wt % aqueous sodium chloride solution (2.2 kg/kg). The organic phase was distilled to 8 L/kg Compound IV under atmospheric pressure to remove water. The distillation was continued by adding ethyl acetate to maintain a constant volume until the water content in the organic was <0.4 wt %. The batch temperature was adjusted to 58-62° C. and charged with tetrahydrofuran (0.79 kg/kg). The batch was seeded with Compound IV (0.23 wt %, prepared in a previous batch or through self-seeding) to ensure nucleation and then charged with tetrahydrofuran (1.44 kg/kg) over a period of at least 1 h maintaining the temperature between 58 and 62° C. On completion of the addition, the batch was cooled to 0-2° C. over a period of at least 2 h and agitated for an additional 2 h. The slurry was filtered and the cake washed with THF/EtOAc (20% v/v, 1.98 kg/kg) followed by n-heptane (2.16 kg/kg). The cake was dried at 50° C. until the criteria for residual heptane was met. The product was obtained as a white to off-white solid in >75% yield and >99.5 AP.

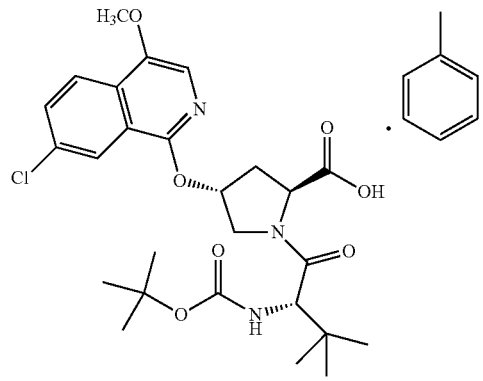

Preparation of Compound (II)

Compound IV (1.10 equiv.) was dissolved in MeTHF (15 L/kg) at 65° C. The warm solution was transferred to a second vessel containing a 20 wt % solution of potassium tert-butoxide in THF (3.50 equiv, 0.20 excess equiv.) then rinsed with MeTHF (2 L/kg) to form the potassium salt of Compound IV. Compound III (solid, 1 equiv., limiting reagent) was charged to the suspension containing the potassium salt of Compound IV followed by MeTHF (1 L/kg). The resultant suspension was heated to 50° C. and held at 50° C. until the reaction was deemed complete by HPLC and/or Raman. Upon completion of the reaction the mixture was cooled to 20° C. and quenched with an aqueous solution of sodium phosphate monobasic, 4M, (6.25 equiv.). The biphasic mixture was agitated for 30 min and the phases were separated. The organic phase was distilled under vacuum to a volume of 13.5 L/kg and toluene (16.5 L/kg) was added. The organic phase was washed twice with a pH 6.3 buffer solution (sodium phosphate monobasic/sodium phosphate dibasic solution) and the organic phase was sampled. HPLC confirmed removal of the starting material and impurities. After removal of the impurities the organic phase was distilled to 15 L/kg under vacuum followed by a constant volume distillation with the addition of toluene to maintain the volume at 15 L/kg. The distillation was deemed complete when MeTHF was ≤1.0 vol %. Acetic acid (0.15 L/kg) was added to the slurry followed by MeTHF (1 L/kg) and the batch was heated to 95° C. and aged at least 15 min. to obtain full dissolution of the solids. The solution was cooled to 74° C., seeded with crystals of Compound II (prepared in a previous batch or through self-seeding) (0.010 kg/kg) to facilitate crystallization and aged at 74° C. for at least 60 min. The slurry was cooled to 20° C. over at least 4 h then aged at 20° C. for 5 h. The slurry was filtered and washed twice with toluene (6 L/kg) followed by n-heptane (6 L/kg). The wet cake was dried at 50° C. under vacuum until the n-heptane was ≤0.2 wt %. The product was isolated as a white to off-white solid in >75% yield and >99.5 AP.

Preparation of Compound I

A reactor charged with THF (5 L/kg), Compound II (1 equiv., limiting reagent), and Compound V (1.05 equiv., prepared by methods known in the art, for example, WO2013028471) was cooled to 0° C. Charged N,N-Diisopropylethylamine (DIPEA) (0.92 equiv.) followed by 1-(3-Dimethylaminopropyl)-3-ethylcarbodiimide Hydrochloride (EDAC) (1.15 equiv.). On completion of the addition the reaction mixture was warmed to 20° C. and aged for 3 h or until the reaction was deemed complete by HPLC. Upon completion of the reaction charged water (5 L/kg) and MTBE (7.5 L/kg) and agitated the biphasic mixture for 30 min. Allowed the phases to separate and removed the aqueous phase. Washed the organic phase with 2N sodium acetate (5 L/kg) followed by water (5 L/kg) until the organic layer contained <0.2 RAP of residual pTSA. Transferred the organic phase to a clean reactor and distilled under vacuum to a volume of 5 L/kg. Continued to distill the batch maintaining the volume at 5 L/kg while charging SDA 2B 200 Proof. The distillation was deemed complete when the residual THF was <1 vol %. On completion of the distillation charged Ethanol SDA 2B 200 Proof (3.0 L/kg) and heated the batch to 60° C. to dissolve any solids that may have precipitated during the distillation. Cooled the batch to 50° C. and seeded with Compound I (prepared in a previous batch or through self-seeding) (0.50 wt %). Cooled the batch to 20° C. over 1.5 h while wet milling and aged the batch at 20° C. for 1 h. Stopped the wet milling and cooled the batch to 0° C. over 1 h and aged at 0° C. for at least 1 h. Filtered the slurry and washed the cake twice with cold (0° C.) Ethanol SDA 2B 200 Proof (1.8 L/kg). Dried the wet cake at 70° C. until the residual EtOH was <0.1 wt %. The product was isolated as a white to off-white solid in >75% yield and >99.5 AP.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A process for preparing a compound of formula (I),

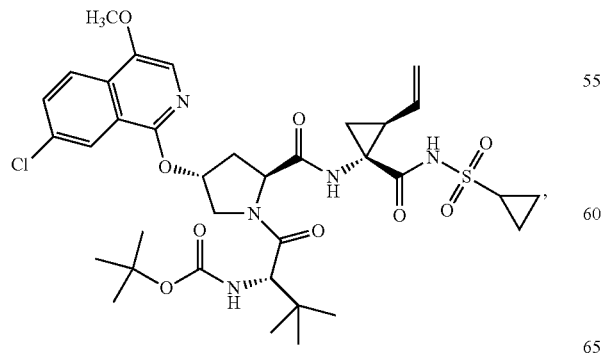

the process comprising:

(a) treating a compound of formula (III)

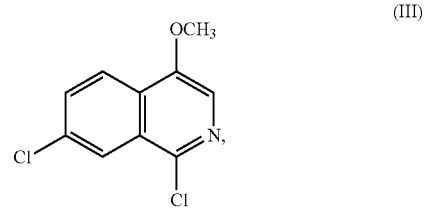 [SMILES: COc1cnc(Cl)c2cc(Cl)ccc12]

with a compound of formula (IV)

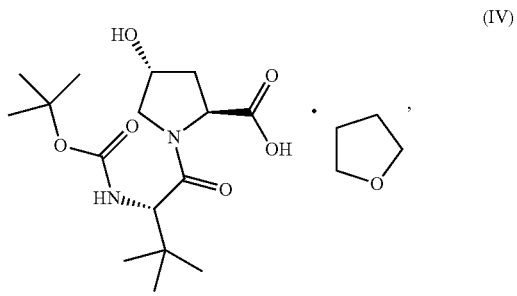 [SMILES: CC(C)(C)OC(=O)N[C@H](C(=O)N1C[C@H](O)C[C@H]1C(=O)O)C(C)(C)C ; C1CCOC1]

in the presence of potassium tert-butoxide; and (b) crystallizing the product of step (a) from toluene, to form a compound of formula (II)

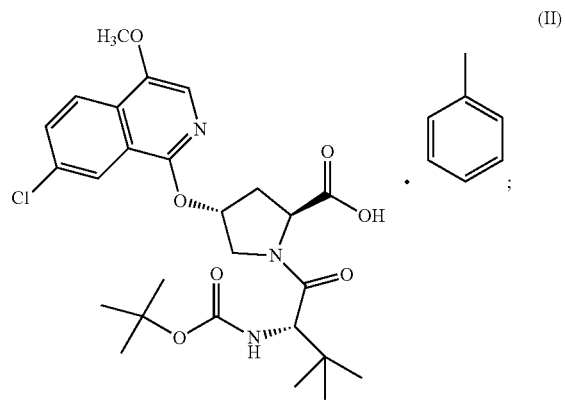

(c) treating the compound of formula (II) with a compound of formula (V),

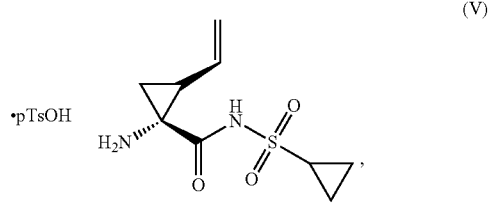

and 1-ethyl-3-(3-dimethylaminopropyl)carbodiimide in the presence of diisopropylethylamine; and (d) crystallizing the compound of formula (I).

2. A process for preparing a compound of formula (I),

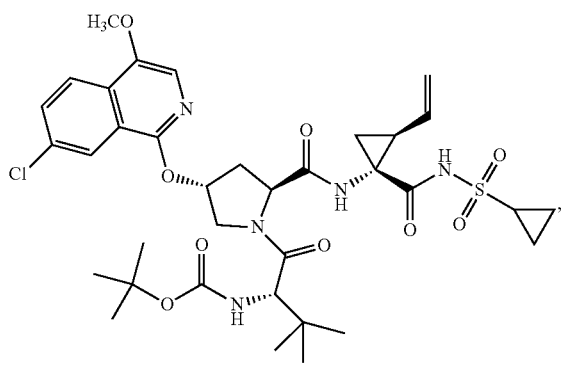

the process comprising:
(a) treating a compound of formula (III)

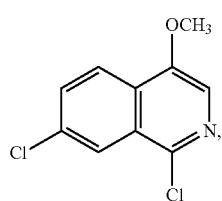

with a compound of formula (IV)

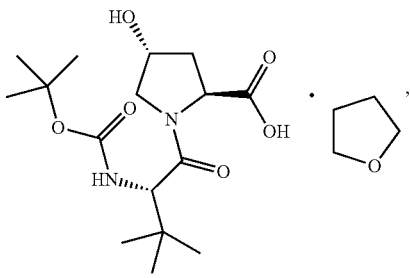

in the presence of potassium tert-butoxide;
(b) quenching step (a) with sodium phosphate monobasic;
(c) isolating then distilling the organic phase of step (b); and
(d) crystallizing the product of step (a) from toluene, to form a compound of formula (II)

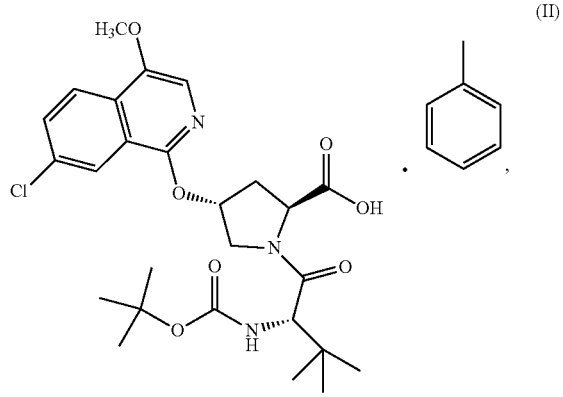

(e) treating the compound of formula (II) with a compound of formula (V),

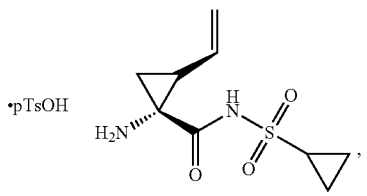

and 1-ethyl-3-(3-dimethylaminopropyl)carbodiimide in the presence of diisopropylethylamine;
(f) treating the reaction mixture of step (a) with water and methyl tert-butyl ether;
(g) isolating then distilling the organic phase of step (f); and
(h) crystallizing the product of step (f) to form the compound of formula (I).

* * * * *